(12) United States Patent
Jump (10) Patent No.: US 11,874,264 B2
(45) Date of Patent: Jan. 16, 2024

(54) SYSTEMS AND METHODS FOR REPORTING PERFORMANCE OF AGRICULTURAL INPUTS

(71) Applicant: Heritage Landscape Supply Group, Inc., McKinney, TX (US)

(72) Inventor: Bruce A. Jump, Grabill, IN (US)

(73) Assignee: Heritage Landscape Supply Group, Inc., McKinney, TX (US)

( * ) Notice: Subject to any disclaimer, the term of this patent is extended or adjusted under 35 U.S.C. 154(b) by 916 days.

(21) Appl. No.: 16/530,347

(22) Filed: Aug. 2, 2019

(65) Prior Publication Data

US 2021/0033587 A1 Feb. 4, 2021

(51) Int. Cl.
*G01N 33/00* (2006.01)
*A01C 21/00* (2006.01)
(Continued)

(52) U.S. Cl.
CPC ....... *G01N 33/0098* (2013.01); *A01C 21/007* (2013.01); *A01G 3/00* (2013.01); *A01G 25/16* (2013.01); *G06Q 50/02* (2013.01)

(58) Field of Classification Search
CPC .... G01N 33/0098; A01C 21/007; A01G 3/00; A01G 25/16; G06Q 50/02
See application file for complete search history.

(56) References Cited

U.S. PATENT DOCUMENTS 3,462,257 A * 8/1969 Timmons ............. A01N 43/707
544/182
6,463,431 B1 10/2002 Schmitt
(Continued)

FOREIGN PATENT DOCUMENTS

WO WO-2016040678 A1 * 3/2016 ........... A01B 79/005
WO WO-2019063274 A1 * 4/2019 ........... A01B 79/005

OTHER PUBLICATIONS

Hancock Seed, "Hancock Seed Company Home Page", http://www.hancockseed.com, snapshot of Oct. 29, 2006 downloaded from www.archive.org using the Wayback, (Accessed Jul. 19, 2011), 3 pages.
(Continued)

*Primary Examiner* — John E Breene
*Assistant Examiner* — Xiuqin Sun
(74) *Attorney, Agent, or Firm* — Norton Rose Fulbright US LLP (57) ABSTRACT

A computer-implemented method for reporting performance of an agricultural input for a plant involves: storing in a computer database a set of agricultural inputs, plants for which the agricultural inputs are used, performance attributes of the agricultural inputs, historical agricultural input performance values, and a relative significance of each of the agricultural inputs for the performance attribute. A computer processor is used to receive a plant selection; receive an attribute to be targeted for the plant selection; identify a plurality of agricultural inputs for affecting the targeted attribute for the plant using the historical agricultural input performance values; rank the plurality of agricultural inputs for affecting the targeted attribute for the selected plant using the relative significance associated (Continued)

therewith; and display the plurality of agricultural inputs and corresponding ranks for the received attribute associated with the selected plant.

6 Claims, 8 Drawing Sheets

(51) Int. Cl.
*G06Q 50/02* (2012.01)
*A01G 3/00* (2006.01)
*A01G 25/16* (2006.01)

(56) References Cited

U.S. PATENT DOCUMENTS

| | | | |
|---|---|---|---|
| 8,424,243 B1* | 4/2013 | Narciso | A01N 3/00 47/2 |
| 9,087,022 B2 | 7/2015 | Jump | |
| 9,582,778 B2* | 2/2017 | Dlott | G06Q 50/02 |
| 10,332,220 B2 | 6/2019 | Jump | |
| 2005/0125260 A1* | 6/2005 | Green | G06Q 40/08 705/4 |
| 2006/0112123 A1 | 5/2006 | Clark et al. | |
| 2009/0106272 A1 | 4/2009 | Jump et al. | |
| 2010/0192242 A1 | 7/2010 | Li | |
| 2021/0219550 A1* | 7/2021 | Van Rooijen | A01N 25/22 |

OTHER PUBLICATIONS

Morris, Kvin N. et al., "A Guide to NTEP Turfgrass Ratings", http://ntep.org/reports/ratings.htm, snapshot of Sep. 28, 2006 downloaded from www.archive.org using the Wayback Machine, (Accessed Jul. 19, 2011), 4 pages.

Patton, Aaron P., "Selecting zoysiagrass cultivators: Turf quality and stress tolerance", Research GCM, May 2010, pp. 90-95.

Wayback Machine, , "Calculating a weighted average using Excel Functions", http://web.archive.org/web/20060924050200/http://www.meadinkent.co.uk!xlwtdavg.htm,snapshot of Sep. 24, 2006 downloaded from www.archive.org, (Accessed on Aug. 25, 2012), 1 page.

Wherley, B. G. et al., "Low-input Performance of Zoysiagrass (*Zoysia* spp.) Cultivators Maintained under Dense Tree D", HortScience vol. 46 No. 7, 2011, pp. 1033-1037.

Yue, Chengyan et al., "User Preferences for Accessing Publically Available Turfgrass Cultivar Performance Data", Funded by Specialty Crop Research Initiative Competitive Grant of the USDA's National Institute of Food and Agriculture, Aug. 27, 2019, 12 pages.

* cited by examiner

| DISEASE | ANTHRACNOSE | | | | | |
|---|---|---|---|---|---|---|
| | TOP LSD PERFORMANCE RANK | | | | | |
| FUNGICIDE | 1 | 2 | 3 | 4 | 5 | 6 |
| Headway | 100.0% | 0.0% | 0.0% | 0.0% | 0.0% | 0.0% |
| Banner MAXX | 60.0% | 3.3% | 13.3% | 13.3% | 6.7% | 3.3% |
| Insignia | 58.3% | 0.0% | 16.7% | 25.0% | 0.0% | 0.0% |
| Heritage TL | 54.2% | 20.8% | 12.5% | 12.5% | 0.0% | 0.0% |
| Daconil Ultrex | 33.3% | 11.1% | 22.2% | 22.2% | 5.6% | 5.6% |
| Instrata | 16.7% | 0.0% | 33.3% | 50.0% | 0.0% | 0.0% |
| Daconil Weatherstik | 16.7% | 0.0% | 33.3% | 41.7% | 8.3% | 0.0% |

FIG. 5

| ACTIVE INGREDIENT | ATTRIBUTES | | | | | |
|---|---|---|---|---|---|---|
| FUNGICIDE | DOLLAR SPOT | BROWN PATCH | QUALITY SCHEDULE A | SPRING GREEN UP | GENETIC COLOR | TOP PERFORMANCE INDEX |
| 5 | 46.5% | 54.7% | 90.9% | 82.2% | 92.2% | 73.3% |
| 13 | 42.7% | 79.9% | 81.9% | 78.7% | 76.2% | 71.9% |
| 18 | 81.3% | 68.6% | 84.2% | 76.3% | 41.4% | 70.4% |
| 16 | 78.8% | 98.0% | 14.4% | 70.3% | 74.4% | 67.2% |
| 3 | 36.1% | 77.2% | 79.7% | 60.6% | 79.7% | 66.7% |
| 9 | 71.8% | 95.7% | 61.1% | 64.3% | 17.0% | 62.0% |
| 14 | 57.5% | 78.4% | 28.4% | 92.2% | 52.7% | 61.8% |
| 12 | 74.1% | 49.5% | 0.3% | 92.8% | 84.1% | 60.2% |
| 11 | 99.5% | 44.6% | 63.8% | 69.7% | 10.4% | 57.6% |
| 19 | 57.2% | 87.8% | 43.5% | 25.7% | 72.9% | 57.4% |
| 15 | 77.7% | 58.4% | 29.9% | 63.1% | 54.9% | 56.8% |
| 4 | 92.0% | 8.4% | 71.3% | 86.0% | 13.2% | 54.2% |
| 1 | 2.2% | 86.2% | 53.0% | 88.1% | 13.7% | 48.6% |
| 10 | 64.9% | 77.5% | 1.6% | 16.6% | 61.4% | 44.4% |
| 6 | 13.5% | 23.5% | 15.6% | 71.1% | 78.2% | 40.4% |
| 20 | 0.7% | 16.3% | 51.2% | 31.3% | 98.4% | 39.6% |
| 17 | 14.6% | 21.5% | 50.9% | 40.1% | 52.7% | 36.0% |
| 2 | 32.6% | 17.7% | 30.1% | 8.1% | 87.6% | 35.2% |
| 8 | 0.8% | 42.5% | 50.5% | 9.8% | 62.7% | 33.3% |
| 7 | 3.9% | 10.8% | 37.9% | 56.7% | 27.5% | 27.4% |

FIG. 6

| Average of PERFORMANCE INDEX SCORE | | | REPORT # | | | | |
|---|---|---|---|---|---|---|---|
| FUNGICIDE | RATE | SPRAY INTERVAL DAYS | R-101 | R-102 | R-103 | R-104 | % TPI |
| 1 | A | 7 | 25.1% | 55.2% | 58.9% | 46.5% | 46.4% |
| | | 14 | 40.3% | 49.5% | 52.2% | 75.9% | 54.5% |
| | | 21 | 64.6% | 66.3% | 34.7% | 75.4% | 60.3% |
| | | 28 | 99.9% | 43.7% | 32.1% | 21.3% | 49.2% |
| | B | 7 | 80.9% | 40.7% | 93.1% | 45.6% | 65.1% |
| | | 14 | 73.0% | 81.1% | 80.2% | 6.3% | 62.6% |
| | | 21 | 96.9% | 68.0% | 37.1% | 63.3% | 66.3% |
| | | 28 | 78.9% | 12.8% | 45.4% | 77.1% | 53.6% |
| | C | 7 | 67.5% | 84.3% | 32.3% | 8.0% | 48.0% |
| | | 14 | 28.4% | 91.8% | 66.4% | 8.0% | 48.6% |
| | | 21 | 51.2% | 15.9% | 90.8% | 12.2% | 42.5% |
| | | 28 | 22.3% | 27.8% | 69.5% | 33.3% | 38.2% |
| 2 | A | 7 | 56.9% | 42.6% | 55.9% | 73.6% | 57.2% |
| | | 14 | 55.6% | 33.4% | 80.5% | 62.9% | 58.1% |
| | | 21 | 40.1% | 33.9% | 48.2% | 49.5% | 42.9% |
| | | 28 | 69.4% | 5.0% | 90.6% | 27.3% | 48.1% |
| | B | 7 | 12.1% | 31.9% | 11.8% | 31.0% | 21.7% |
| | | 14 | 38.8% | 76.0% | 18.5% | 60.2% | 48.4% |
| | | 21 | 11.1% | 7.2% | 83.8% | 69.5% | 42.9% |
| | | 28 | 1.1% | 9.6% | 90.5% | 1.3% | 25.6% |
| | C | 7 | 33.9% | 46.2% | 44.9% | 86.9% | 53.0% |
| | | 14 | 65.0% | 22.9% | 87.7% | 19.6% | 48.8% |
| | | 21 | 54.2% | 50.8% | 12.0% | 83.4% | 50.1% |
| | | 28 | 40.3% | 8.6% | 97.7% | 9.1% | 38.9% |
| 3 | A | 7 | 9.2% | 24.4% | 9.4% | 11.5% | 13.6% |
| | | 14 | 63.2% | 16.6% | 80.8% | 74.1% | 58.7% |
| | | 21 | 84.7% | 87.5% | 87.0% | 22.4% | 70.4% |
| | | 28 | 12.3% | 30.6% | 0.3% | 12.7% | 14.0% |
| | B | 7 | 43.3% | 84.0% | 94.9% | 3.6% | 56.5% |
| | | 14 | 22.5% | 21.4% | 90.8% | 72.8% | 51.9% |
| | | 21 | 1.6% | 70.9% | 53.9% | 74.0% | 50.1% |
| | | 28 | 56.8% | 40.3% | 0.6% | 0.3% | 24.5% |
| | C | 7 | 1.4% | 71.8% | 50.5% | 66.7% | 47.6% |
| | | 14 | 57.2% | 3.0% | 85.7% | 92.2% | 59.5% |
| | | 21 | 43.2% | 55.6% | 66.2% | 94.0% | 64.7% |
| | | 28 | 62.4% | 74.7% | 51.6% | 94.4% | 70.7% |
| 4 | A | 7 | 3.4% | 14.4% | 50.3% | 3.2% | 17.8% |
| | | 14 | 59.0% | 72.9% | 53.1% | 65.7% | 62.6% |
| | | 21 | 65.1% | 4.2% | 67.2% | 23.9% | 40.1% |
| | | 28 | 28.6% | 35.7% | 17.8% | 49.7% | 32.9% |
| | B | 7 | 96.5% | 63.1% | 29.3% | 88.0% | 69.2% |
| | | 14 | 0.5% | 23.1% | 23.3% | 78.1% | 31.3% |
| | | 21 | 91.2% | 3.5% | 11.1% | 54.3% | 40.0% |
| | | 28 | 15.9% | 18.4% | 0.4% | 6.4% | 10.3% |
| | C | 7 | 82.3% | 99.3% | 44.5% | 99.4% | 81.4% |
| | | 14 | 83.7% | 11.6% | 1.8% | 89.0% | 46.5% |
| | | 21 | 11.8% | 35.4% | 80.4% | 79.5% | 51.8% |
| | | 28 | 73.8% | 93.0% | 59.1% | 87.9% | 78.4% |
| % TPI | | | 47.4% | 43.1% | 52.6% | 49.8% | 48.2% |

SYSTEMS AND METHODS FOR REPORTING PERFORMANCE OF AGRICULTURAL INPUTS

FIELD OF THE INVENTION

Implementations are directed to systems and methods for reporting the effectiveness of agricultural inputs according to a target plant.

BACKGROUND

Soil, seeds and plants are treated with agricultural inputs, for instance, pesticides, to control the spread of plant disease. In one example, turfgrass growing in a field may be treated with fungicides to control the spread of disease. However, there are many species of turfgrass seeds, and each species produces a grass that has unique characteristics or attributes. For example, some species can produce grasses that vary in color, leaf width, moisture requirements, and density (i.e., number of living plants in 1"×1" area). These and other factors associated with the turfgrass can impact the effectiveness of agricultural inputs on the plant. Growers face these same problems when cultivating other plants, such as crop plants.

Moreover, agricultural inputs such as pesticides, fertilizers, micronutrients and adjuvants are commonly applied to plants, soil or seed behave differently when applied to different plants, or when applied at differing rates, time of year, locales, and so on. While these inputs may control the spread of disease or facilitate plant growth, the performance of the inputs can be variable depending on various factors. Vendors such as large agricultural companies often provide information about the performance of their products to provide growers with assurances that the product will perform as desired. However, this information is inherently biased in favor of the vendor's product, and growers encounter difficulty in identifying agricultural inputs that matches their needs in the field.

SUMMARY

Systems and methods herein may be used to report performance of agricultural inputs according to the plant targeted.

According to certain implementations, a computer-implemented method for reporting performance of an agricultural input for a plant involves: using a computer database to store a set of agricultural inputs, plants for which the agricultural inputs are used, performance attributes of the agricultural inputs, historical agricultural input performance values, and a relative significance of each of the agricultural inputs for the performance attribute, where the relative significance of each of the agricultural inputs is relative to a control; and using a computer processor to: receive a plant selection; receive an attribute to be targeted for the plant selection; identify a plurality of agricultural inputs for affecting the targeted attribute for the plant based on the historical agricultural input performance values; rank the plurality of agricultural inputs for affecting the targeted attribute for the selected plant using the relative significance associated therewith; and display the plurality of agricultural inputs and corresponding ranks for the received attribute associated with the selected plant.

In implementations and alternatives, the performance attributes of the agricultural inputs include American Phytopathological Society performance attributes.

In implementations and alternatives, the attribute to be controlled is a plant disease, the agricultural input includes one or more of: a pesticide, a plant growth regulator, a nutrient, an adjuvant, or a combination thereof, the plant selection includes one or more of a crop plant, a sexually reproducing plant, an asexually reproducing plant, a seed variety, and/or the attribute to be targeted includes one or more of pest control, yield, controlled growth, nutrient uptake.

In implementations and alternatives, the plurality of agricultural inputs are ranked for their historical effectiveness.

In implementations and alternatives, the method further involves providing a rank based on a spray interval.

In implementations and alternatives, the set of agricultural inputs further includes parameters at which the agricultural input was delivered, and the computer processor is further configured to receive a selection of a parameter for delivering the agricultural input and identify the plurality of agricultural inputs therefrom. Such parameters may include one or more of a type of nozzle from which the agricultural input is delivered, a spray volume of the agricultural input, a water volume, a line pressure, frequency of mowing rate, height of cut.

According to further implementations, a computer-implemented method for reporting performance of an agricultural input for a plant involves: using a computer database to store a set of agricultural input types, agricultural input products, plants for which the agricultural inputs are used, performance attributes of the agricultural input products, historical agricultural input product performance values, and a relative significance of each of the agricultural input products, where the relative significance of each of the agricultural input products is relative to a control; and using a computer processor to: receive a first selection of a plant; receive a second selection of a type of agricultural input or a selection of an agricultural input product targeted for the selected plant, the received second selection for affecting an attribute associated with the selected plant; identify a plurality of agricultural input products using the selections based on the historical agricultural input performance values; rank the plurality of agricultural input products for affecting the targeted attribute for the selected plant using the relative significance associated therewith; and display the plurality of agricultural inputs and ranks for the selected plant.

In implementations and alternatives, the method further involves receiving a selection of two or more agricultural input products, and where the plurality of agricultural input products identified include the received selection of the two or more agricultural input products.

According to yet further implementations, a computer-implemented method for predicting performance of an agricultural input for a plant involves using a computer database to store a set of agricultural inputs, plants for which the agricultural inputs are used, performance attributes of the agricultural inputs, and historical agricultural input performance values; and using a computer processor to: receive a plant selection; receive an attribute to be targeted for the plant; identify a plurality of agricultural inputs for affecting the targeted attribute for the plant based on the historical agricultural input performance values; and display on a visual interface a comparison of performance of two or more of the identified agricultural inputs for affecting the targeted attribute for the selected plant as a prediction of performance of the agricultural inputs on the selected plant.

BRIEF DESCRIPTION OF THE DRAWINGS

FIG. 7 illustrates a table generated by the processor in which all fungicides in the same technical reports are compared for their performance across a range of attributes according to certain implementations.

DETAILED DESCRIPTION

Implementations provide systems and methods for reporting performance of a plurality of agricultural inputs based on a user selection of an agricultural parameter such as a plant, an agricultural input, an input type (e.g., chemical family), location, or combinations of agricultural parameters disclosed herein. Aspects of the present disclosure may be particularly useful for growers having an established crop, or a previously selected or purchased plant where the agricultural input is applied. However, implementations may be used by growers in planning stages in order to select seeds and agricultural inputs adapted for the selected seeds, for instance. Growers and other users may gain an understanding of the differences in performance across a number of agricultural inputs in order to select the input predicted to achieve a desired plant performance based on the reported information for the input. The approaches provided herein differ from approaches where selection of turfgrass is facilitated by predicting turfgrass performance disclosed in U.S. 9,087,022, entitled Systems and Methods for Predicting Regional Turfgrass Performance, which issued on Jul. 21, 2105 (the '022 patent). The '022 patent is incorporated herein by reference in its entirety for any useful purpose. Particularly, the approaches disclosed herein provide reports of performance of agricultural inputs (e.g., pesticides, nutrients, plant growth regulators, adjuvants, or combinations thereof) according to an agricultural parameter (e.g., a selected plant for which the agricultural input is to be applied or a selected attribute to be controlled). For instance, in the case of turfgrass, implementations may provide a report on a pesticide's performance on a turfgrass variety using the systems and methods described herein. In contrast, the '022 patent discloses the turfgrass performance based on a geography where the turfgrass has historically been grown.

Systems and methods use historical agricultural input performance information to report performance of a number of different agricultural inputs when applied to the same plant or different plants to provide a user with information about agricultural inputs that may be useful for maintaining, growing, or improving plant health. This may enable users to make an informed selection of an agricultural input based on a selected plant or plants.

Implementations use historical reports on agricultural inputs to provide a computer system and method for determining the intersectionality of agricultural inputs and attributes and their impact on performance. These intersections are between any or all of the active ingredient, application rate, frequency of application, plant species, plant variety, nozzle type, water spray volume, as well as other parameters disclosed herein.

Figure 1:
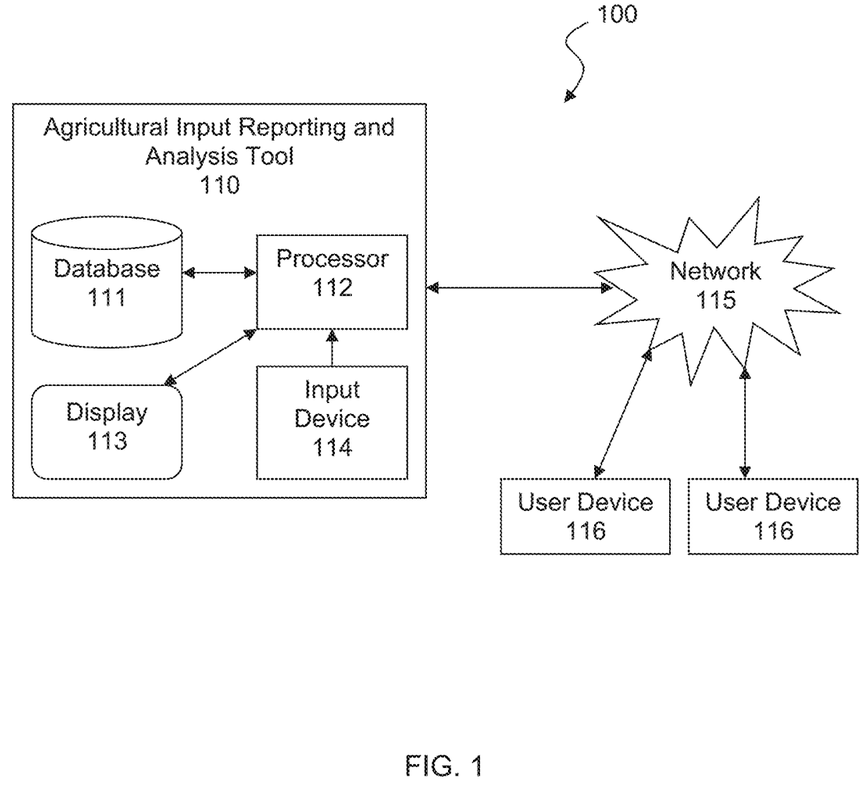
FIG. 1 is a block diagram of a computer system for reporting the performance of agricultural inputs according to certain implementations.

FIG. 1 is a block diagram of a computer system 100 for reporting agricultural input performance, according to certain implementations. The system 100 includes an agricultural input reporting and analysis tool 110 with a database 111, a processor 112, a display 113 and an input device 114 (e.g. a keyboard or remote control). In some implementations, the agricultural input reporting and analysis tool 110 may be one or more general purpose computers, special purpose computers or both.

The database 111 is a relational database configured to store the information required to report on the performance of the agricultural inputs in relation to agricultural selections, e.g., a selected plant or plants. The information stored may include agricultural inputs, plants for which the agricultural inputs are used, performance attributes of the agricultural inputs, historical agricultural input performance values, and a relative significance of each of the agricultural inputs for the performance attribute. The relative significance of each of the agricultural inputs is relative to a control.

Agricultural inputs stored in the database 111 include but are not limited to: pesticides (e.g., herbicides, fungicides, insecticides, nematicides, and bactericides), plant growth regulators, nutrients (e.g., fertilizers, micronutrients), adjuvants and combinations. In some implementations, the agricultural inputs include commercially available products. Such products may be combination of two or more agricultural inputs that have been configured to address one or more performance attributes. The inputs may be categorized in a variety ways including by product type, e.g., disease or diseases targeted, chemical family, vendor name, regional availability, price, and so on.

Plants that are treated with the agricultural inputs and stored in the database 111 can include but are not limited to crop plants (e.g., soy, corn, grass), sexually reproducing plants (e.g., flowers and trees), asexually reproducing plants, a seed variety (e.g., seeds for plants that have not yet been planted, or that have been planted but are identified by their seed variety by those of skill). The plants may be categorized by their genus and species, region grown, vendor name, price and so on.

Performance attributes of the agricultural inputs stored in the database 111 can include but are not limited to: disease control, growth, controlled growth, and nutrient uptake. Disease control attributes may include but are not limited to percent control of disease such as: percent control of brown patch, percent control of cold tolerance, percent control of dollar spot, percent control of leaf spot, percent control of necrotic ring spot, percent control of red thread, percent control of Gray Leaf Spot, percent control of crown and stem rust, percent control of shade/powdery mildew, percent control of summer patch, percent control of summer stress. Growth control attributes may include but are not limited to growth and establishment in the presence of high nitrogen, low nitrogen, low potassium/phosphorus and so on. Other performance attributes may include but are not limited to: aggressiveness and recovery, color, compaction tolerance, drought tolerance, early spring green up, insect resistance, fast establishment, height/moving frequency, insect tolerance, leaf texture, low maintenance, low mowing height, mountain west quality, mowing quality, Pacific Northwest quality, quality ratings, salt tolerance, shade tolerance, sod-shear strength, and wear tolerance.

Historical agricultural input performance values stored in the database 111 may be derived from literature, particularly published agricultural studies, e.g., scientific journals, replicated studies, peer reviewed journals, which may be sourced from the American Pathological Society, or may be from reported information on agricultural studies that may not necessarily be published. These studies provide numerical, tabular, or graphical information about plant responses to agricultural inputs applied. For instance, a percent control by a fungicide on one or various crop plants may be provided. The studies may additionally include statistical information on whether the response, e.g., improvement, is statistically significant relative to a control group. Where multiple agricultural inputs are compared against one another, the statistical information includes information on the relative rankings of each agricultural input relative to the other. This information is useful when considering which product to use for a selected plant when addressing one attribute to be targeted for the plant, e.g., disease; however, locating information specific to the user's needs by manually or electronically searching for study results is difficult. In addition, due to the ubiquitous nature of agricultural inputs, a significant number of studies are performed on just one crop plant to combat one disease. A user performing an electronic search may locate one or more studies, but the ability of the user to interpret the results of potentially hundreds of studies is implausible. The computer system 100 of the present disclosure is used to solve this problem. The database 111 includes the historical agricultural input information, thereby enabling information to be stored, retrieved and processed by the processor 112 for these historical studies performed. Such information includes agricultural inputs, the plants studied, the attribute studied, e.g., condition to be controlled, the results of the studies, and a ranking value calculated by the processor 112 for the agricultural input product that provides information about the ranking of the agricultural input against others or against a control. For instance, an agricultural input may be ranked by the processor 112 based calculating an average of its performance across the different studies stored within the database, and may be ranked against other agricultural inputs having a calculated average computed in the same manner. The relative significance of each of the agricultural inputs may be relative to a control, e.g., a common control across the different studies.

In one example, the relative significance of each of the agricultural inputs for the performance attributes stored in the database 111 is generated by the processor 112 identifying and extracting the performance of the agricultural inputs for a particular plant type (e.g., one plant variety) from each of a plurality of studies of the agricultural input, and that may have been conducted for a number of different plants (e.g., multiple plant varieties) including the particular plant type, ranking the different agricultural inputs studied within the particular study, comparing the performance of the agricultural input for the one particular plant type across the various studies, and ranking the performance of the agricultural input for the plant type using the information from the various studies. The statistical significance for the performance of an agricultural inputs against other agricultural inputs in each individual study is typically determined relative to a control (e.g., water). Across the various studies, the control may be the same or may differ. Where the control differs, the results may be normalized.

Implementations accordingly involve extracting relative performance data for agricultural inputs from publications reporting on comparison studies of one or a plurality of agricultural inputs. Comparison studies report the performance of one or more inputs relative to a control, typically water. The input performance may be relative to other inputs (e.g., head-to-head comparison), relative to the input's performance across a number of different plants, relative to different geographies, relative to different plant diseases, relative to different spray parameters, relative to industry average, or a combination. Where multiple inputs are studied, the studies commonly involve reporting the results of the various inputs after having been applied to the same plant (or seed or soil), in the same geography, using the same spray parameters thus analyzing the agricultural inputs under the same conditions and enabling side-by-side comparisons of the efficacy of the agricultural inputs for a given condition. Where one input is studied, the studies commonly involve reporting the results of the input's performance (e.g., disease control) across a number of plants (or seeds or soils), or across different geographies, or using different spray parameters, while retaining the other variables at a constant (e.g., where different spray parameters are studied, the constants could include the plant and the geography). Of course, these studies may also report on multiple inputs and their performance across multiple plants, across multiple diseases across multiple spray parameters, across multiple geographies, and so on. Other comparison studies for the agricultural inputs can also be understood by a person of skill. Such publications reporting on the comparison studies are published by the American Phytopathological Society, the American Society of Agronomy, as well as others. The comparison studies may generally report on the effectiveness of the input on disease control, particularly, pesticides including fungicides, herbicides, insecticides; but may also report on the effectiveness of agricultural inputs such as plant nutrients and adjuvants, for example. For combatting plant pests, these studies commonly report on the effectiveness of an agricultural input on controlling pests for a given plant. For instance, one study may compare 7 different agricultural inputs for controlling dollar spot on turfgrass. While the results of one study may be helpful for a grower to understand a particular instance of the efficacy of different inputs, dollar spot on turfgrass is a common problem and is widely studied, with the number of reports on this problem alone reaching into the thousands. These studies report on the performance of a given input differently, and often times one input performs worse or the same against a grouping of inputs in one study and performs the best in another study of the same grouping of inputs. Because of the large number of studies, the differing results for the inputs from study-to-study, and due to the changing demands of the grower (e.g., climate, specific type of plant to be grown, specific type of pest to be controlled, spray parameters, etc.), the grower viewing published studies is not provided with sufficient information to make an informed decision for their growing needs, and certainly the grower cannot reasonably predict the performance of a given agricultural input viewing publications with disparate study parameters and conflicting results.

According to one implementation, the extracted study information for the agricultural inputs is analyzed by the processor 112 to rank the inputs according to their statistical significance relative to the other inputs in the study. Study results commonly report on the input performance using a numerical value accompanied by a letter associated with a statistical calculation from the Waller-Duncan k-ratio t test (e.g., sequential letters "a", "b", "c", "d", "e", "f", "g", "h", "i", "j", and so on up to "z", and combinations of sequential letters "a, b", "a, b, c", "b, c, d", "c, d", "d, e, f, g" and so on). In a particular example, the letters assigned in connection with Waller-Duncan k-ratio t test numbers for an agricultural input value are extracted with other agricultural input information (e.g., identify of the input, purpose of the study, geography, spray parameter) and analyzed. In a given study, the significance letters will range from one to 26 sequential letters beginning with the letter "a", commonly three sequential letters (e.g., "a", "b", "c") or more will be present in the published study. The letter associated with the control, commonly "a" but sometimes multiple letters such as "a, b", indicates the performance of the control studied, and the other letters adjacent to the agricultural inputs studied indicates the performance of the input relative to the control. Where the input significance letter is the same as the control, e.g., "a", this means the input did not perform better than the control. The higher the letter is away from the control letter, e.g., further away from the letter "a", the better performer the input. For an input value assigned "c", compared to an input value assigned "b", with the control assigned "a", the input value assigned "c" is a better performer compared to the input assigned "b", but both input values indicate the associated inputs perform better than the control "a". The study includes a highest letter, which indicates the best performing agricultural input relative to the other inputs studied. For instance, significance letters that extend to "e" for a study will indicate the best performing input by assigning an "e" to the statistical performance for the input. The processor 112 analyzes the different significance letters, identifies the letter that is furthest away from "a", and assigns the inputs studied a ranking according to their significance letters and respective to the range of letters in the study results. For a study with significance letters a-g, the input value(s) assigned "g" will be the best or first ranked input, e.g., "1", the input value(s) assigned "f" will be assigned the next best or second ranked input, e.g., "2", the input value(s) assigned "e" will be assigned the subsequent ranking or third ranked input, e.g., "3", and so on up to the last or worst ranked input value(s), either 6 or 5 depending on whether the input performed the same or worse than the control, e.g., where the control is assigned "a". For studies where a numerical value is assigned multiple statistical letters, e.g., "e, f, g", the processor 112 assigns the highest letter to the agricultural input, i.e., "g", and then ranks that input against the other inputs according to this highest letter. The processor 112 thus assigns a relative significance for each of the inputs in the study and stores this information in the database 111 for the published studies. The processor 112 then generates rankings of the agricultural inputs relative to others according to the disclosure.

Figure 5:
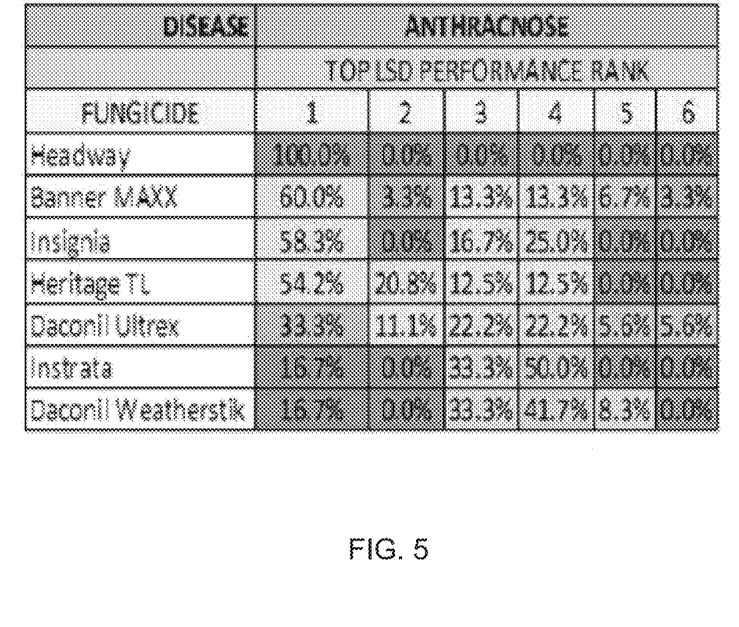
FIG. 5 illustrates a table of top performing agricultural inputs generated by the processor and transmitted according to the present disclosure.

The table of FIG. 5 illustrates a graphical display of the top performing agricultural inputs (fungicides) generated according to the present disclosure. For instance the system 100 may be used to generate the graphical display using the study information stored in the database 111 where the fungicides were studied for their effectiveness against disease (anthracnose) across a group of studies analyzed by the processor 112. As illustrated, at least one of these included a significance letter of "f", i.e., the sixth sequential letter in the alphabet, and the rankings for this fungicide range from 1-6 based on the studies analyzed by the processor 112, with the best performing input "f" ranked "1". Based on the analysis of the group of publications for the fungicides evaluated for their effectiveness of anthracnose, Headway was the top performer, i.e., ranked number 1, in all of the studies; Banner MAXX was the best performer in 60 percent of the studies; Insignia was the best performer in 58% of the studies, and so on. For Banner MAXX, aside from being the best performer in 60% of the studies, it ranked second in 3.3%, third in 13.3%, fourth in 13.3%, fifth in 6.7% and sixth in 3.3% of the studies.

In addition to the significance letter for the agricultural input from the published studies, the processor 112 and stores in the database 111 the attribute studied (e.g., disease, yield, growth as well as other disclosed attributes), plant (e.g., plant species, plant variety, crop type, seed type), agricultural input product name, vendor, chemical family, researcher identity, university identity.

In some implementations attribute values may be characterized as having an effectiveness over a period of time. Inputs may be applied once per season, twice per season, or once every 7, 14, 21, 28 or 42 days. In one example, the intervals may be once or twice per season for turfgrass. In another example, disease control may be studied and provided as percent control of a disease by an agricultural input, such as a fungicide, over a time period, such as 7 days, 14 days, 21 days or 28 days, and the processor 112 may extract this information from the studies.

In some implementations, the processor 112 extracts and the database 111 stores study results that include parameters at which the agricultural input was delivered. The parameters may include spray parameters such as nozzle type from which the agricultural input is delivered, flow rate (e.g., psi), volume (e.g., gallons per minute), spray interval (e.g., 0, 7, 14, 21, 28 days; 0, 16, 29, 35, 43, 51, 57 days; 0, 16, 29, 35, 51 days; 0, 16, 29, 43, 57 days; and so on), water volume, a line pressure, and other parameters such as height of cut (HOC) (e.g., 0.14, 0.18, 0.24, 0.5, 0.75, 1.0, 3.5, 5.5 in.), mowing rate (e.g., daily, twice weekly, three times weekly, etc.), and FRAC code (Fungicide Resistance Action Committee). FRAC is a group of specialists that identify active ingredients by common properties and families. Fungicides in the same family or FRAC code typically should not be used over and over in a spray program, and should be rotated with other FRAC code families.

Other information stored by the database 111 may include historical growing year when the study was conducted, location (e.g., region, state, county, zip code) where the agricultural input was studied, planting season (e.g., spring, summer, fall, winter). Further, the database 111 may store information related to availability and pricing of the grass species or varieties generally, as well as price and availability within particular regions, may be included in the grass seed identification information.

In some implementations, the computer processor 112 is configured to receive a selection of multiple study parameters stored by the database 111 for use in generating reports of performance of the agricultural input based on parameters of interest.

The processor 112 of the agricultural input reporting and analysis tool 110 is configured to execute operations for reporting performance of agricultural inputs described herein. In addition, the processor 112 is configured to execute instructions for receiving, retrieving and updating agricultural input performance information stored in the database 111. For example, the processor 112 and the database 111 may be periodically updated with agricultural input information derived from published reports such as journal publications disclosed herein. The processor 112 may also be configured generate graphical displays of the reporting information, and to transmit content to a display 113 such as agricultural input rankings, listings of the rankings, graphs, charts, and displays enabling a user to enter selections for causing the processor to generate and display such content. Further, the processor 112 is communicatively coupled to the input device 114 and is configured to receive input such as the user selections. The display 113 may be a conventional display device such as a computer monitor, and the input device 114 may be a conventional keyboard or a remote control.

While the reporting and analysis tool 110 of system 100 may be used for reporting performance of agricultural inputs, in some implementations the system 100 may be communicatively coupled to a communications network 115 for enabling a number of user devices 116 to enter user input and receive information on the performance of the agricultural inputs from the system 100.

Figure 2:
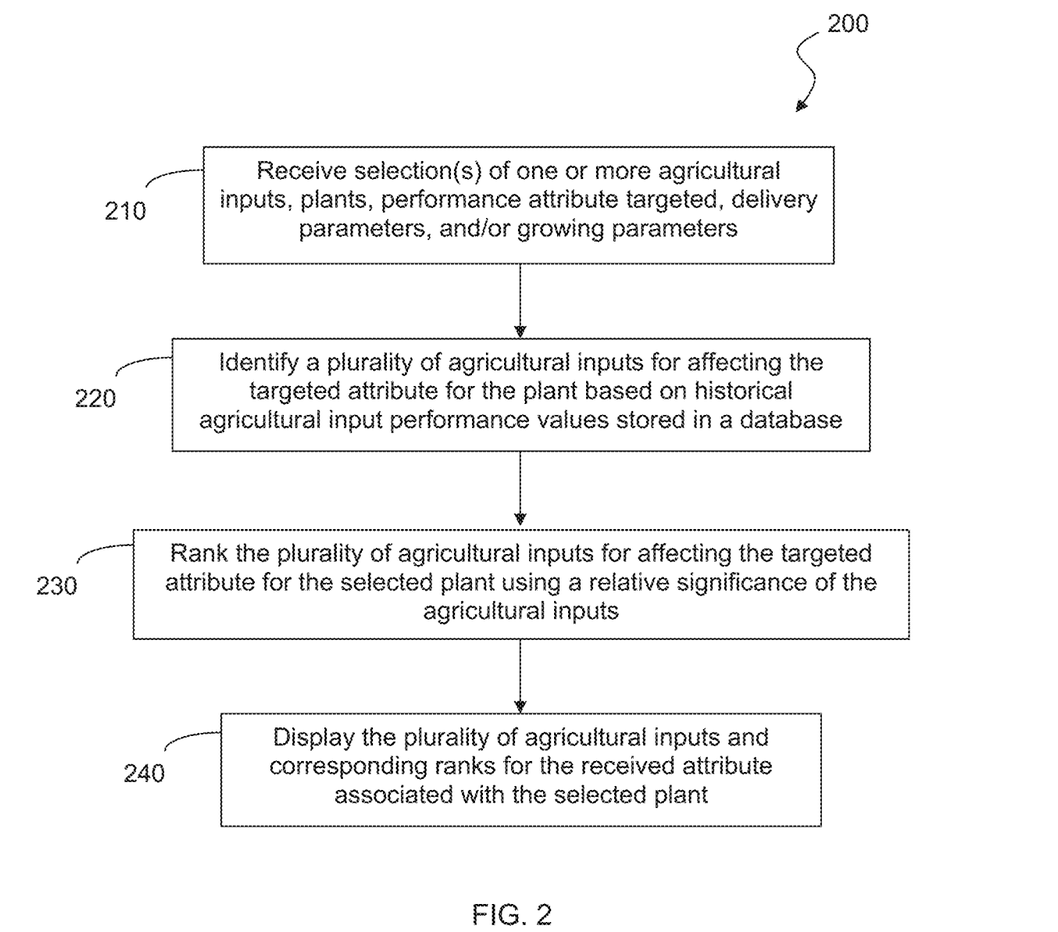
FIGS. 2-4 are a flow charts of a method for reporting performance of agricultural inputs for a plant according to certain implementations.

FIG. 2 illustrates a method 200 of using the system 100 for reporting performance of agricultural inputs of interest for a selected plant in which the processor 112 executes instructions for performing the operations therein. In operation 210, one or more selections are received for one or more of agricultural inputs, plants, performance attribute targeted, delivery parameters, growing parameters (e.g., geography, season), or any of the study parameters extracted by the processor 112 or stored in database 111. For example, a user may select a plant and an attribute to be targeted. The attribute targeted may include but is not limited to: pest control, yield, controlled growth, nutrient uptake. In another example, a plant selection as well as a selection of an agricultural input type, an agricultural input, or an agricultural input product may be provided. A plant selection may include but is not limited to: crop plant, a sexually reproducing plant, an asexually reproducing plant, a seed variety. The agricultural input may include but is not limited to: a pesticide, a plant growth regulator, a nutrient, an adjuvant, or a combination thereof. In addition, in operation 210, other selections may be made, such as spray parameters, geographies (e.g., region, state, county, zip code), disease, as well as other parameters described herein.

Receipt of the selections may result in the processor 112 identifying relevant information stored in the database 111 and reducing the available options for subsequent selection, when applicable, and display such options for user selection.

Upon receipt of the selections, operation 220 proceeds by identifying a plurality of agricultural inputs for the plant. For instance, where the selections in operation 210 are of a plant and an attribute to be targeted, the inputs identified in operation 220 are based on the historical agricultural input performance values for the selected plant and attribute targeted stored in database 111 as provided herein. Operation 220 identifies a plurality of records stored in the database 111 for a plurality of agricultural inputs that relate to the selection parameters. The agricultural inputs may be identified for instance, by product name, product type, chemical family, and combinations and the records in database 111 may include historical information related to the reported performance of the agricultural input in a given study. Such information includes the rank of the agricultural input for the given study, e.g., "1", "2", "3", "4", "5", "6" and so on. In addition or alternatively, the record may be linked to such historical information and stored in database 111 or retrievable by processor 112 for use in the system 100.

Using the identified information stored in the database 111, the method proceeds to operation 230 where the plurality of agricultural inputs for affecting the targeted attribute for the selected plant are ranked using the relative significance associated therewith. For instance, the ranking for each agricultural input in the plurality of records is retrieved and pooled, and the agricultural inputs are ranked against one another using this pooled information. In some implementations, the input rankings are based on filtered information. For instance, the rankings for an input may be used only when the input was studied side-by-side with another input from the plurality of inputs identified. In another example, the rankings may be applied only when the input was studied in a geography of interest, a spray parameter of interest, and so on. In these examples, the processor 112 may receive user selections for filtering the agricultural input reporting data.

In operation 240 the processor 112 displays the plurality of agricultural inputs and corresponding ranks for the received attribute associated with the selected plant.

Figure 3:
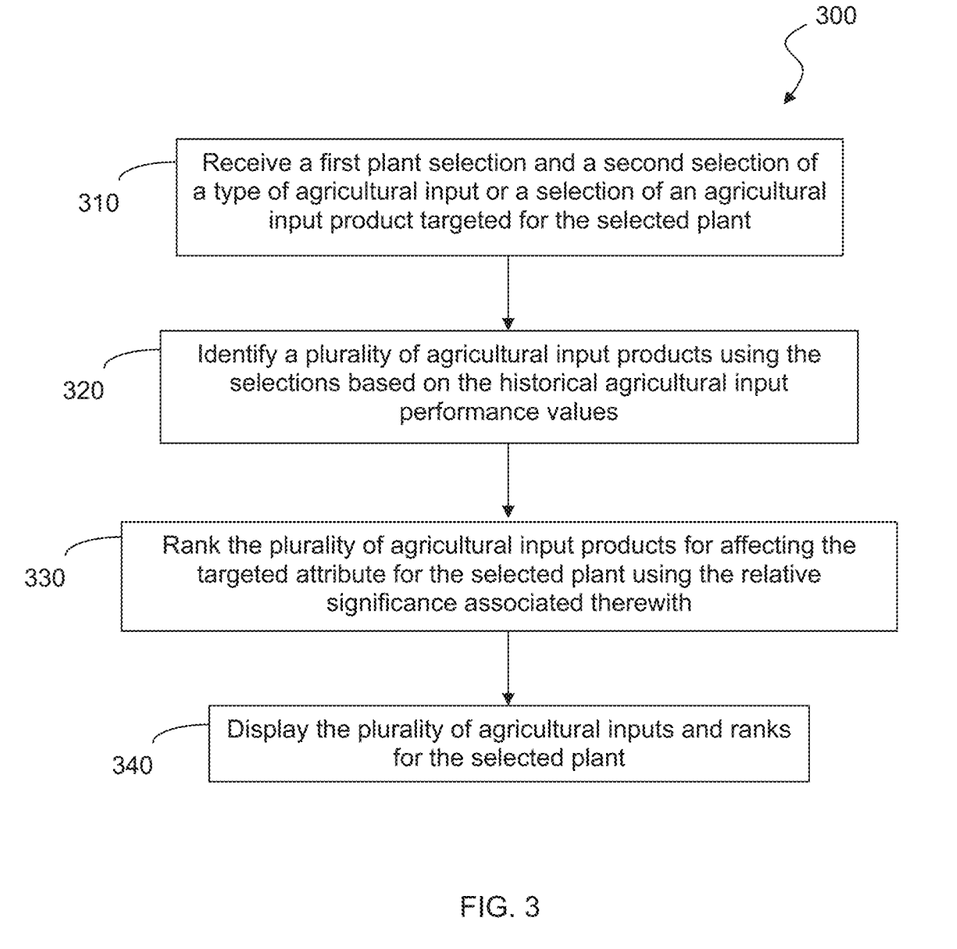

Method 300 illustrated in the flowchart of FIG. 3 provides a further implementation of reporting on the performance of an agricultural input using the system 100. The method of FIG. 3 starts with operation 310, in which the processor 112 receives a first plant selection, as well as a second selection of a type of agricultural input or a selection of an agricultural input product targeted for the selected plant. In this approach, the received second selection is for an input affecting an attribute associated with the selected plant. In operation 320, the processor 112 may identify a plurality of agricultural input products from the database 111 using the selections based on the historical agricultural input performance values. In operation 330, the processor 112 may rank the plurality of agricultural input products for affecting the targeted attribute for the selected plant using the relative significance associated therewith. In operation 340, the processor may display the plurality of agricultural inputs and ranks for the selected plant. In some implementations, method 300 may further involve receiving a selection of two or more agricultural input products, and the processor may identify the plurality of agricultural input products from the database 111 that includes at least one of the received selection of the two or more agricultural input products.

Figure 4:
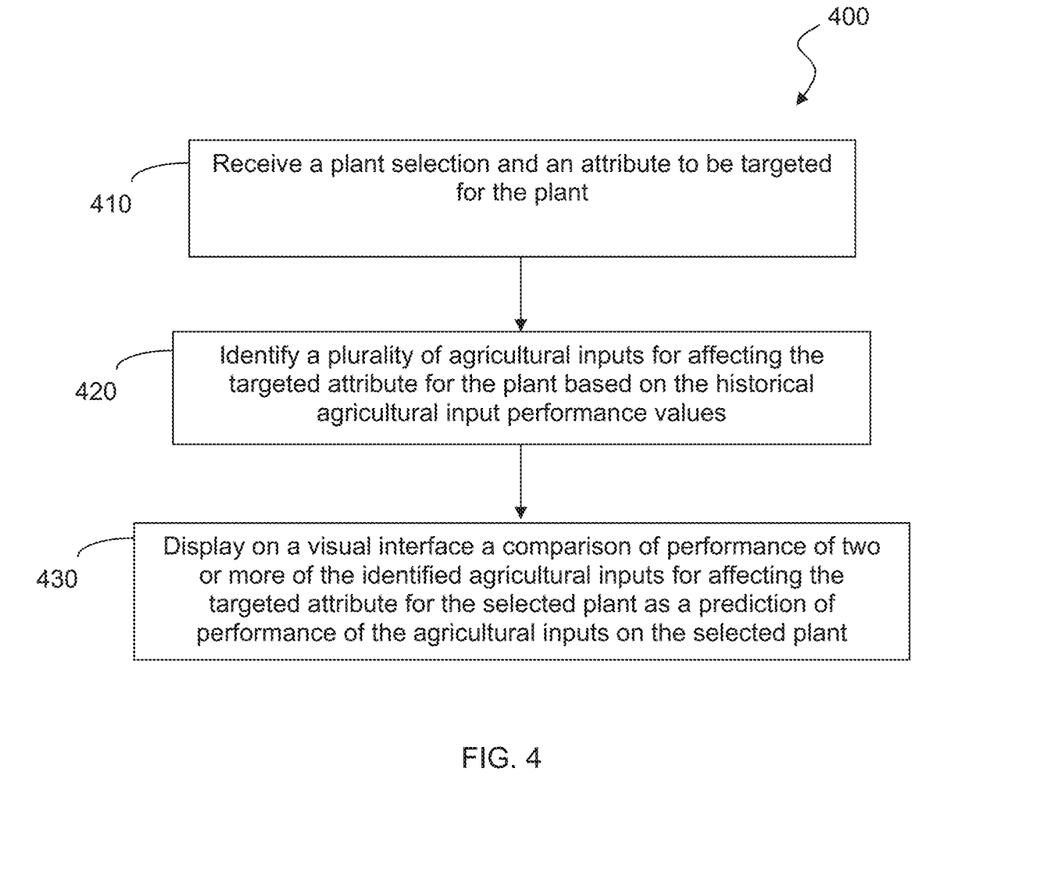

Another approach according to the present disclosure is illustrated in the flowchart of FIG. 4, where the system 100 implements a method 400 for reporting performance of an agricultural input for a plant using the computer database 111 and processor 112. The computer database 111 is used to store a set of agricultural inputs, plants for which the agricultural inputs are used, performance attributes of the agricultural inputs, and historical agricultural input performance values. In operation 410 the computer processor is used to receive a plant selection and an attribute to be targeted for the plant. The method proceeds in operation 420 by the processor 112 identifying a plurality of agricultural inputs for affecting the targeted attribute for the plant based on the historical agricultural input performance values. In operation 430, the processor displays on a visual interface a comparison of performance of two or more of the identified agricultural inputs for affecting the targeted attribute for the selected plant as a prediction of performance of the agricultural inputs on the selected plant.

FIG. 5, discussed previously, illustrates a table of top performing agricultural inputs generated by the processor 112 and transmitted for display, e.g., according to one or more of operations 240, 340, or 430 described herein.

Figure 6:
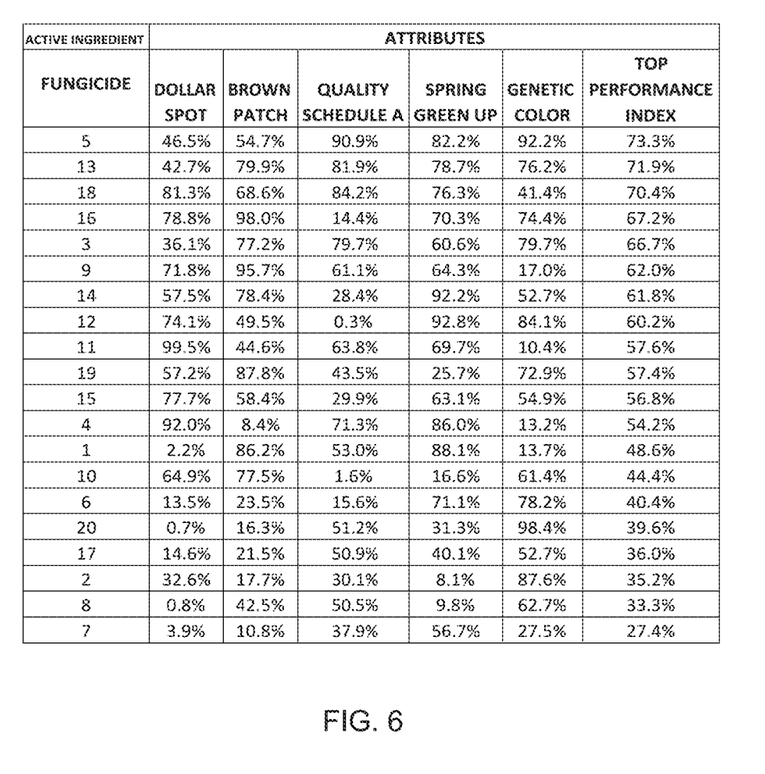
FIG. 6 illustrates a table generated by the processor using the top performing agricultural input information for a plurality of attributes and provides a top performer index based thereon according to certain implementations.

FIG. 6 is another illustration of a table generated by the processor 112$m$ e.g., according to one or more of operations 240, 340, or 430 described herein, and according to certain implementations, in which the top performing agricultural input information is used for a plurality of attributes, and provides a top performer index average based thereon. In FIG. 6 the fungicides as applied to turfgrass are ranked based their performance for each of dollar spot, brown patch, quality, spring green up and genetic color. For instance, fungicide 5 was the top performer for dollar spot control, e.g. ranked "1", in 46.5 percent of the studies that reported on this fungicide; was the top performer for brown patch control in 54.7 percent of the studies that reported on this fungicide; was the top performer for quality in 90.9 percent of the studies that reported on this fungicide; was the top performer for spring green up in 82.2 percent of the studies that reported on this fungicide; was the top performer for genetic color in 92.2 percent of the studies that reported on this fungicide. As shown in FIG. 6, on average for these attributes, fungicide 5 ranked at the top 73.3 percent of the time. For each of the attributes, the number of studies reporting on fungicide 5 can vary. That is, a given study may report on one or more attributes for fungicide 5, but may not necessarily report on all five attributes listed in FIG. 6. Consequently, the system 100 enables the aggregation of information on a variety of different agricultural inputs reported across different studies and displays the performance ranking so that the user can easily identify the best performing inputs for their needs. In FIG. 6, for instance, fungicides 5, 13 and 18, on average, ranked at or above the top performer 70 percent of the time or more in the studies of the five attributes, whereas fungicides 20, 17, 2, 8 and 7 were the top performer less than 40 percent of the time, providing the user with helpful information on the historical performance of these fungicides, which may facilitate fungicide selections.

FIG. 7 is an illustration of a table generated by the processor 112, e.g., according to one or more of operations 240, 340, or 430 described herein, and according to certain implementations in which all fungicides in the same technical reports are compared for their performance across a range of attributes. The fungicides 1-4, were sprayed at different rates (A, B, C), and at different spray intervals (7, 14, 21, and 28 days) and the rank data in four different reports (R-101, R-102, R-103, R-104) averaged across the four different reports. For fungicide 1, sprayed at rate A, with a spray interval of 7 days, fungicide 1 was the top performer in the four different reports, respectively, 25.1, 55.2, 58.9, and 46.5 percent of the time for the attributes within the study. On average, fungicide 1 was the top performer 46.4 percent of the time for across the four reports. Generating rank information according to a spray interval may be helpful for a user to understand frequency of application of the agricultural input that is needed to achieve a desired level of performance, as well as an understanding of overall cost for the input. FIG. 7 provides a predictive model based on probability theory. The higher the Index score in the chart, the higher the probability of high performance, and vice versa for a low score. For example, when a fungicide has a very high index score across the intersectionality of rate, frequency, location, disease attribute, year over year, soil-weather-management conditions at each of these locations (e.g., across different reports), then the fungicide will have a high probability of high performance at most locations.

Figure 8:
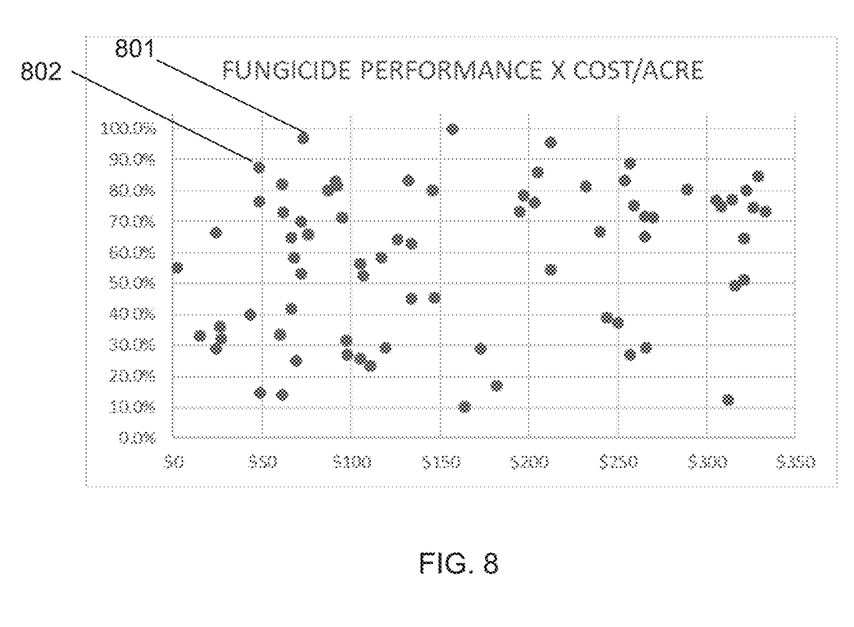
FIG. 8 illustrates a graph generated by the processor where each dot represents a different fungicide as a function of its performance in the top performing index and cost.

FIG. 8 illustrates a graph generated by the processor 112 where each dot represents a different fungicide as a function of its performance in the top performing index and cost. In this figure, the highest performing fungicides are located in the top portion of the graph as the y-axis runs from 0-100%. The lowest cost fungicides are located on the left portion of the graph as the x-axis runs from $0 to $350. As illustrated in FIG. 1, fungicide 801 is a top performing input nearly in 100 percent of the studies reported and has a cost of about $75 per acre. Fungicide 802 is a top performing input in nearly 90 percent of the studies in which the fungicide is reported and has a total cost of about $50 per acre. This may provide helpful information for a grower deciding on their desired performance and cost of application for the input.

In additional or alternative implementations, the plurality of agricultural inputs are ranked for their historical effectiveness. For instance, the agricultural input may improve, stay the same or perform worse over time.

In further implementations, where the database stores parameters at which the agricultural input was delivered, and the computer processor 112 may receive a user selection of a parameter for delivering the agricultural input and identify the plurality of agricultural inputs therefrom. For instance, the parameters may include one or more of a type of nozzle from which the agricultural input is delivered, a spray volume of the agricultural input, a water volume, a line pressure, frequency of mowing rate, height of cut.

This application also hereby incorporates by reference in its entirety U.S. application Ser. No. 11/876,022, filed Oct. 22, 2007, entitled "Methods and Tools for Evaluating a Mixture of Turfgrass Seeds."

In the present disclosure, the methods disclosed may be implemented as sets of instructions or software readable by a device. Further, the specific order or hierarchy of steps in the methods disclosed are examples of sample approaches and the specific order or hierarchy of steps in the method can be rearranged while remaining within the disclosed subject matter. The accompanying method claims present elements of the various steps in a sample order, and are not necessarily meant to be limited to the specific order or hierarchy presented.

The present disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

It is believed that the present disclosure and many of its attendant advantages will be understood by the foregoing description, and it will be apparent that various changes may be made in the form, construction and arrangement of the components without departing from the disclosed subject matter. The form described is merely explanatory, and it is the intention of the following claims to encompass and include such changes.

While the present disclosure has been described with reference to various embodiments, it will be understood that these embodiments are illustrative and that the scope of the disclosure is not limited to them. These and other variations, modifications, additions, and improvements may fall within the scope of the disclosure as defined in the claims that follow.

What is claimed is:

1. A computer-implemented method for predicting performance of an agricultural input for a plant, the method comprising:

storing, in a computer database, agricultural input data corresponding to agricultural inputs, plant data corresponding to plants for which the agricultural inputs are used, performance attribute data corresponding to performance attributes of the agricultural inputs, historical agricultural input performance values, and statistical significance data associated with the performance attribute data and indicative of a performance of an agricultural input relative to a control;

receiving, at a computer processor and via an input device communicatively coupled to the computer processor, a first indication of a plant selection;

receiving, at the computer processor and via the input device, a second indication of an attribute to be targeted for the plant selection;

identifying, via the computer processor, a set of the agricultural input data corresponding to a plurality of agricultural inputs for affecting the attribute for the plant selection based on the historical agricultural input performance values;

ranking, by the computer processor, agricultural inputs corresponding to the set of agricultural input data, based on a probability of an effectiveness of the agricultural inputs to affect the attribute for the plant selection, wherein ranking the agricultural inputs based on the probability of the effectiveness of the agricultural inputs includes ranking the agricultural inputs based on an index score determined based on a frequency of application of the agricultural inputs, a location of use of the agricultural inputs, and weather conditions;

rendering, by the computer processor, on a display device, a graphical display, wherein the graphical display is configured to depict a comparison of performance of two or more of the agricultural inputs for affecting the attribute for the selected plant as the probability of the effectiveness of the agricultural input to affect the attribute for the selected plant; and spraying at least one of the two or more agricultural inputs on the selected plant, the at least one agricultural input selected based on the probability of the effectiveness of the at least one agricultural input to affect the attribute for the selected plant.

2. The method of claim 1, wherein the performance attributes of the agricultural inputs comprise American Phytopathological Society performance attributes.

3. The method of claim 1, wherein the attribute is a plant disease.

4. The method of claim 1, wherein the agricultural input comprises one or more of a pesticide, a plant growth regulator, a nutrient, an adjuvant, or a combination thereof.

5. The method of claim 1, wherein the first indication corresponding to the plant selection comprises one or more of a crop plant, a sexually reproducing plant, an asexually reproducing plant, or a seed variety.

6. The method of claim 1, wherein the attribute to be targeted comprises one or more of pest control, yield, controlled growth, nutrient uptake, or a combination thereof.

* * * * *